United States Patent
Sakyu et al.

(10) Patent No.: US 6,235,951 B1
(45) Date of Patent: May 22, 2001

(54) METHOD FOR PRODUCING 1,1,1,3,3-PENTAFLUOROPROPANE

(75) Inventors: Fuyuhiko Sakyu, Miyoshi; Satoshi Yoshikawa, Moroyama; Yasuo Hibino, Shiki; Yoshihiko Gotoh, Miyoshi; Ryouichi Tamai, Kamifukuoka, all of (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 08/752,879

(22) Filed: Nov. 20, 1996

(30) Foreign Application Priority Data

Jan. 17, 1996 (JP) .................................................. 8-005971
Aug. 23, 1996 (JP) .................................................. 8-222004
Aug. 28, 1996 (JP) .................................................. 8-226638

(51) Int. Cl.$^7$ ........................... C07C 17/00; C07C 19/08; C07C 17/08
(52) U.S. Cl. ........................ 570/156; 570/163; 570/165; 570/167; 570/168
(58) Field of Search .................................. 570/156, 163, 570/165, 167, 168

(56) References Cited

U.S. PATENT DOCUMENTS

| | | | |
|---|---|---|---|
| 2,787,646 | 4/1957 | Haszeldine . | |
| 2,942,036 | 6/1960 | Smith et al. . | |
| 5,146,018 | * 9/1992 | Kellner et al. ........................ | 570/156 |
| 5,155,082 | * 10/1992 | Tung et al. ............................ | 502/228 |
| 5,574,192 | * 11/1996 | VanDerPuy et al. ................. | 570/167 |
| 5,608,127 | * 3/1997 | Gumprecht ............................ | 570/170 |
| 5,616,819 | * 4/1997 | Boyce et al. .......................... | 570/167 |
| 5,659,093 | * 8/1997 | Takubo et al. ........................ | 570/167 |
| 5,710,352 | * 1/1998 | Tung ...................................... | 570/166 |

FOREIGN PATENT DOCUMENTS

WO96/01797  1/1996  (WO) .

OTHER PUBLICATIONS

Henne et al., "Hydrofluorination in the Presence of Boron Fluroide", J. Am. Chem. Soc., 1948, vol. 70, pp. 758–760.*
L. Knunyants, et al., "Reactions of Fluoro Olefins; Communication 13. Catalytic Hydrogenation of Perfluoro Olefins", English Translation of Izvestiya Akademii Nauk SSSR, Otdelenie Khimicheskikh Nauk, No. 8, pp. 1412–1418, Aug. 1960.

Albert L. Henne et al., "Hydrofluorination in the Presence of Boron Fluoride", J. Am. Chem. Soc., 1948, vol. 70, pp. 758–760.

Martin Kotora et al., "Selective Additions of Polyhalogenated Compounds to Chloro Substituted Ethenes Catalyzed by a Copper Complex", Accepted Jan. 7, 1991, React. Kinet. Catal. Lett., vol. 44, No. 2, 415–419 (1991).

Martin Kotora et al., "Addition of tetrachloromethane to halogenated ethenes catalyzed by transition metal complexes", Journal of Molecular Catalysis, 77 (1992), pp. 51–60.

E.N. Zil'berman et al., "Synthesis fo Liquid Telomers of Vinyl Chloride with Carbon Tetrachloride", Translated from Zhurnal Organicheskoi Khimii, vol. 3, No. 12, pp. 2151–2156, Dec., 1967.

* cited by examiner

*Primary Examiner*—John Kight
*Assistant Examiner*—Raymond Covington
(74) *Attorney, Agent, or Firm*—Evenson, McKeown, Edwards & Lenahan, P.L.L.C.

(57) ABSTRACT

The present invention relates to a method for producing 1,1,1,3,3-pentafluoropropane. This method includes the steps of (a) adding hydrogen fluoride to 1-chloro-3,3,3-trifluoropropene in the presence of an addition catalyst to obtain 1,1,1,3-tetrafluoro-3-chloropropane; and (b) disproportionating the 1,1,1,3-tetrafluoro-3-chloropropane into the 1,1,1,3,3-pentafluoropropane and 1,1,1-trifluoro-3,3-dichloropropane, in the presence of a disproportionation catalyst. This method is a useful method for producing 1,1,1,3,3-pentafluoropropane in an industrial scale, because its steps (a) and (b) are respectively superior in selectivity and yield. According to the invention, 1-chloro-3,3,3-trifluoropropene may be produced by a method including a step of reacting 1,1,1,3,3-pentachloropropane with hydrogen fluoride in a gas phase in the presence of a fluorination catalyst. This method is useful, because yield of 1-chloro-3,3,3-trifluoropropene is high.

15 Claims, No Drawings

METHOD FOR PRODUCING 1,1,1,3,3-PENTAFLUOROPROPANE

BACKGROUND OF THE INVENTION

This invention relates to a method for producing 1,1,1,3,3-pentafluoropropane, which is useful as a foaming agent for foaming substances such as polyurethane, a refrigerant, and the like.

There are several conventional methods for producing 1,1,1,3,3-pentafluoropropane. For example, JP-A-Hei-6-256235 discloses a method for producing 1,1,1,3,3-pentafluoropropane from $CF_3$—$CClX$—$CF_2Cl$ where X is hydrogen or chlorine, by catalytic hydrogenation. A preferable catalyst for this method is a common hydrogenation catalyst. U.S. Pat. No. 2,942,036 discloses a method of hydrogenating 1,2,2-trichloropentafluoropropane to produce 1,1,1,3,3-pentafluoropropane or 1,1,3,3,3-pentafluoro-1-propene or mixtures thereof. A catalyst for this method is palladium carried on activated carbon. These two methods mentioned hereinabove are superior in conversion and selectivity. However, these catalysts deteriorate considerably in these methods. Furthermore, it is necessary to prepare the raw material(s) of these methods in advance. Thus, these methods may not be suitable for the production of 1,1,1,3,3-pentafluoropropane in an industrial scale.

There is disclosed, in published English translation (pp. 1312–1317) of Izvestiya Akademii Nauk SSSR, Otdelenie Khimicheskikh Nauk, No. 8, pp. 1412–1418, August, 1960 (CA 55, 349f), a method for producing 1,1,1,3,3-pentafluoropropane by hydrogenating 1,1,3,3,3-pentafluoro-1-propene in the presence of Pd—$Al_2O_3$. However, it is difficult to find the raw material of this method (i.e., 1,1,3,3,3-pentafluoro-1-propene) on the market.

There is another method for producing 1,1,1,3,3-pentafluoropropane by fluorinating 1,1,1,3,3-pentachloropropane in a liquid phase in the presence of a catalyst (see WO96101797). However, this method is relatively low in selectivity and yield.

Unlike 1,1,1,3,3-pentalfluoropropane mentioned hereinabove, there is known another compound, 1-chloro-3,3,3-trifluoropropene, which is useful as an intermediate of medicines, of agricultural chemicals, of functional materials, and of fluorohydrocarbons. This compound is obtained, for example, by the following first to fifth processes. In the first process, 1,1,1-trifluoropropane is chlorinated to obtain 1,1,1-trifluoro-3,3-dichloropropane, and then this compound is dehydrochlorinated by an alcoholic basic compound to produce 1-chloro-3,3,3-triuoropropene (see J. Am. Chem. Soc., 1942, 64, 1158). In the second process, hydrogen chloride is added to 3,3,3-trifluoropropyne to produce 1-chloro-3,3,3-trifluoropropene (see J. Chem. Soc., 1952, 3490). The second process is superior in conversion and selectivity. However, it is difficult to obtain the raw material of the second process (i.e., 3,3,3-trifluoropropyne) on the market. In the third process, 3-chloro-1,1,1-trifluoro-3-iodopropane is dehydroiodinated by alcoholic potassium hydroxide to produce 1-chloro-3,3,3-trifluoropropene (see J. Chem. Soc., 1953, 1199). In the fourth process, 3-bromo-3-chloro-1,1,1-trifluoropropane is dehydrobrominated by an alcoholic potassium hydroxide (see R. N. Haszeldine, J. Chem. Soc., 1951, 2495). The third and fourth processes are superior in conversion and selectivity. However, according to these processes, there is needed more than stoichiometric amount of potassium hydroxide, and it is necessary to prepare the raw materials in advance. Thus, there are problems to apply these processes to an industrial scale production. In the fifth process, 1,3,3,3-tetrachloropropene is fluorinated by hydrogen fluoride in the presence of an antimony catalyst (see U.S. Pat. No. 2,787,646). In the fifth process, there are a problem that it is difficult to obtain the raw material of the reaction on the market, and another problem that the yield of 1-chloro-3,3,3-trifluoropropene is poor for the industrial scale production.

SUMMARY OF THE INVENTION

It is an object of the present invention to provide a method for producing 1,1,1,3,3-pentafluoropropane, which method is free of the above-mentioned drawbacks.

It is a specific object of the present invention to provide a method for producing 1,1,1,3,3-pentafluoropropane, which method is high in selectivity and yield.

According to a first aspect of the present invention, there is provided a first method for producing 1,1,1,3,3-pentafluoropropane, comprising steps of;

(a) adding hydrogen fluoride to 1-chloro-3,3,3-trifluoropropene in the presence of an addition catalyst to obtain 1,1,1,3-tetrafluoro-3-chloropropane; and (b) disproportionating said 1,1,1,3-tetrafluoro-3-chloropropane into said 1,1,1,3,3-pentafluoropropane and 1,1,1-trifluoro-3,3-dichloropropane, in the presence of a disproportionation catalyst.

The first method of the present invention is a useful method for producing 1,1,1,3,3-pentafluoropropane in an industrial scale, because its steps (a) and (b) are respectively superior in selectivity and yield.

According to the first aspect of the present invention, there is further provided a first modification of the first method, for producing 1,1,1,3-tetrafluoro-3-chloropropane, comprising a step of adding hydrogen fluoride to 1-chloro-3,3,3-trifluoropropene in the presence of an addition catalyst.

According to the first aspect of the present invention, there is still further provided a second modification of the first method, for producing 1,1,1,3,3-pentafluoropropane, comprising a step of disproportionating 1,1,1,3-tetrafluoro-3-chloropropane into said 1,1,1,3,3-pentafluoroprop ane and 1,1,1-trifluoro-3,3-dichloropropane, in the presence of a disproportionation catalyst.

According to a second aspect of the present invention, there is provided a second method for producing 1-chloro-3,3,3-trifluoropropene, comprising a step of reacting 1,1,1,3,3-pentachloropropane with hydrogen fluoride in a gas phase in the presence of a fluorination catalyst. The raw material of the second method, 1,1,1,3,3-pentachloropropane, is easily obtained by one of the after-mentioned conventional methods. Furthermore, yield of 1-chloro-3,3,3-trifluoropropene is high, and therefore the second method is useful as an industrial-scale method for producing 1-chloro-3,3,3-trifluoropropene.

According to the present invention, the first and second methods bay be combined, thereby to produce 1,1,1,3,3-pentafluoropropane from 1,1,1,3,3-pentachloropropane.

DESCRIPTION OF THE PREFERRED EMBODIMENTS

In accordance with the first aspect of the present invention, there will be described in detail the above-mentioned first method for producing 1,1,1,3,3-pentafluoropropane, as follows. The relevant parts of the following descriptions of the first method also apply to the above- mentioned first and second modifications of the first method.

In the first method, each of the steps (a) and (b) may be conducted by a batch operation or by a continuous operation in which the reactants are continuously supplied to a reactor and in which the reaction product is continuously removed therefrom. Of these, the continuous operation is preferably taken.

In the first method, the addition catalyst used in the step (a) is preferably at least one compound selected from antimony halides, tin halides, titanium halides and boron halides. For instance, it is assumed that boron trifluoride and hydrogen fluoride form a coordinated complex therebetween. Thereby, the degree of ionic character of H-F bond is increased. With this, the addition catalyst is assumed to catalyze addition reactions between olefins and hydrogen fluoride (see A. L. Henne et al., J. Am. Chem. Soc., 1948, 70, 758). Examples of antimony halides to be used as the addition catalyst are antimony pentachloride, antimony pentabromide, antimony pentaiodide, antimony pentafluoride, antimony trichloride, antimony tribromide, and antimony triiodide Of these, antimony pentachloride and antimony trichloride are preferable examples. Examples of tin halides to be used as the addition catalyst are tin tetrachloride, tin tetrabromide, tin tetraiodide and tin tetrafluoride. Of these, tin tetrachloride is the most preferable example. Examples of titanium halides to be used as the addition catalyst are titanium tetrachloride, titanium tetrabromide, titanium tetraiodide and titanium tetrafluoride. Of these, titanium tetrachloride is the most preferable example. Examples of boron halides to be used as the addition catalyst are boron trichloride, boron tribromide, boron triiodide, and boron trifluoride. Of these, boron trifluoride and boron tribromide are the most preferable examples.

In the first method, the disproportionation catalyst used in the step (b) is preferably at least one compound selected from antimony halides and aluminum halides. Examples of these antimony halides are the same as those of the antimony halides used as the addition catalyst. Examples of the aluminum halides are aluminum chloride, aluminum bromide, and aluminum iodide. Of these, aluminum chloride is the most preferable example.

In the first method, it is preferable to use the same at least one antimony halide for both of the steps (a) and (b), because both of the steps (a) and (b) can be conducted in a single reactor. The addition reaction of the step (a) and the disproportionation reaction of the step (b) are represented by the following reaction formulas (1) and (2), respectively.

$$CF_3CH=CCH+HF \rightarrow CF_3CH_2CClFH \quad (1)$$

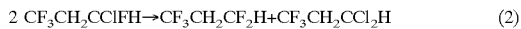

$$2\ CF_3CH_2CClFH \rightarrow CF_3CH_2CF_2H+CF_3CH_2CCl_2H \quad (2)$$

The by-product of the disproportionation reaction, 1,1,1-trifluoro-3,3-dichloropropane, may be dehydrochlorinated into 3-chloro-1,1,1-trifluoropropene, depending on the reaction conditions, particularly on the temperature condition.

In the step (a) of the first method, it is sufficient to use hydrogen fluoride in an amount of within a range of from about 1 to about 2 moles per mol of 1-chloro-3,3,3-trifluoropropene. If it is less than this range, the degree of addition of hydrogen fluoride to 1-chloro-3,3,3-trifluoropropene may not become high. If it is greater than this range, conversion of 1-chloro-3,3,3-trifluoropropene may not improve further, as compared with a case in which it is within this range. Furthermore, this may not be economically advantageous from the viewpoint of the recovery of the unreacted hydrogen fluoride.

In the first method, concentration of the addition catalyst is preferably from 0.1 to 50 mol % and more preferably from 2 to 20 mol %, based on the total number of moles of 1-chloro-3,3,3-trifluoropropene. If it is less than 0.1 mol %, rate of the addition reaction may become too small. If it is greater than 50 mol %, the production of tarry substances made up of high-boiling-point compounds may increase too much.

The addition reaction is conducted at a temperature preferably ranging from -10 to 150° C. and more preferably ranging from 20 to 100° C. If the temperature is lower than -10° C., the conversion of 1-chloro-3,3,3-trifluoropropene is not sufficient. On the other hand, if the temperature is higher than 150° C., the amount of tarry material may increase.

In the first method, concentration of the disproportionation 10 catalyst is preferably from 0.1 to 50 mol % and more preferably from 2 to 20 mol %, based on the total number of moles of 1,1,1,3-tetrafluoro-3-chloropropane. If it is less than 0.1 mol %, reaction rate of the disproportionation may become too small. If it is greater than 50 mol %, the amount of undesirable by-products made up of olefins and/or high molecular weight compounds may increase.

The temperature of the disproportionation reaction is preferably from 0 to 150° C. and more preferably from 30 to 100° C. If it is lower than 0° C., yield of 1,1,1,3,3-pentafluoropropane may become too low. If it is higher than 150° C., the tar's production may become too much, while the catalyst may deteriorate considerably.

In the steps (a) and (b) of the first method, a solvent may be added to the reaction system in order to adjust the reactions thereof and to suppress deterioration of the addition and disproportionation catalysts. Examples of this solvent are saturated fluorocarbons, chlorofluorocarbons, and perfluorocarbons, which are inert in the reactions.

In the step (a) of the first method, 1-chloro-3,3,3-trifluoropropene and hydrogen fluoride may be introduced separately or together into a reactor. It is possible to get the right balance between the amount by mol of an organic matter obtained as the reaction products and the amount by mol of the organic matter used as the raw material, by adjusting temperature of a reflux condenser for cooling a gas flowing from the reactor.

In the first method, pressure needed to conduct the reactions of the steps (a) and (b) varies depending on the reaction temperature, and this pressure is not particularly limited as long as the reaction mixture in the reaction vessel is maintained in the form of liquid. The pressure is preferably from 1 to 100 kg/cm²G and more preferably from 1 to 20 kg/cm²G.

A reactor used in the first method is preferably made of a material such as Hastelloy, stainless steel, Monel metal or nickel, or a material lined with one of these metals, tetrafluoroethylene resin, chlorotrifluoroethylene resin, vinylidene fluoride resin or PFA resin.

In the first method, the obtained 1,1,1,3,3-pentafluoropropane may be purified by a conventional method for purifying reaction products obtained by the fluorination. In this purification, for example, acid fraction is removed, followed by washing using a basic aqueous solution and/or water, drying, and distillation.

In the following, there will be described in detail the above- mentioned second method for producing 1-chloro-3,3,3-trifluoropropene, in accordance with the second aspect of the present invention.

As stated above, the second method comprises a step of reacting 1,1,1,3,3-pentachloropropane with hydrogen fluoride in a gas phase in the presence of a fluorination catalyst.

A raw material of the second method, 1,1,1,3,3-pentachloropropane, may be produced, for example, by the following conventional first, second, and third processes. In the first process, vinylidene chloride is reacted with chloroform in the presence of copper-amine catalyst (see M. Kotora et al. (1991) React. Kinet. Catal. Lett., Vol. 44, No. 2, pp. 415–419). In the second process, carbon tetrachloride is reacted with vinyl chloride in the presence of copper-amine catalyst (see M. Kotora et al. (1992) J. of Molecular Catalysis, Vol. 77, pp. 51–60). In the third process, carbon tetrachloride is reacted with vinyl chloride in an isopropanol solvent, in the presence of a ferrous chloride catalyst (see E. N. Zil'berman et al. (1969) J. of Org. Chem. USSR, Vol. 3, pp. 2101–2105).

In the second method, the fluorination catalyst has first and second preferable examples that are respectively a partially fluorinated aluminum oxide and a stainless steel that has been treated with hydrogen fluoride. Hereinafter, these preferable examples will respectively be referred to as the first and second fluorination catalysts. Aluminum oxide has various morphologies depending on the manner of preparing the same. Aluminum oxide used in the second method is not limited to a particular type, and γ-alumina can easily be found on the market and thus is preferably used for that. Of γ-alumina, there is preferably used in the second method an active alumina that is generally used for supporting catalyst, is relatively large in specific surface area, and is superior in heat resistance. Examples of stainless steel used in the second method are ferrite-type stainless steel (SUS 430) and austenite-type stainless steels (SUS 304, 304L, 316, and 316L). Preferable examples of the same are stainless steels that are in the forms of wool, net, wire and thin tube, and a distillation tower's filler that is prepared from one of these stainless steels into an arbitrary shape.

In the second method, the manner of preparing the first and second fluorination catalysts is not particularly limited. The first fluorination catalyst may be prepared by sequential steps of (a) preparing aluminum oxide from the precursor in the form of sphere or rod; and (b) treating the aluminum oxide with a fluorine-containing compound by spraying of a hydrofluoric acid solution, by immersion into this solution, or by bringing the aluminum oxide into contact with a gas that as hydrogen fluoride, fluorohydrocarbon or chlorofluorohydrocarbon under an elevated temperature. The second fluorination catalyst is prepared by immersing stainless steel into a hydrofluoric acid solution, followed by drying, or by filling a reaction tube with stainless steel and then allowing hydrogen fluoride to flow through the reaction tube.

In the second method, the fluorination catalyst has a third preferable example that is at least one compound of at least one metal selected from the group consisting of aluminum, chromium, manganese, nickel, and cobalt. Hereinafter, this example will be referred to as the third fluorination catalyst. Examples of the at least one compound are oxide, fluoride, chloride, fluorochloride, oxyfluoride, oxychloride, and oxyfluorochloride. The at least one compound may be carried on a carrier such as an aluminum compound or active carbon. Examples of this aluminum compound are aluminum oxide, fluoride, chloride, fluorochloride, oxyfluoride, oxychloride, and oxyfluorochloride.

In the second method, the manner of preparing the third fluorination catalyst is not particularly limited. When the at least one compound is not carried on a carrier, the at least one compound may be prepared, as follows. At first, a metal hydroxide is precipitated from a solution of a compound of the at least one metal, using a basic substance. After that, this metal hydroxide is turned into a metal oxide, and then this metal oxide is partially or completely modified by halogen, using hydrogen fluoride, hydrogen chloride, chlorofluorohydrocarbon, and the like. In contrast, when the at least one compound is carried on a carrier, the carrier may be immersed into a solution of the at least one compound, or alternatively this solution may be sprayed on the carrier. The carrier may be, for example, an aluminum oxide such as γ-alumina or an alumina that has previously been modified by hydrogen fluoride, hydrogen chloride, chlorofluorohydrocarbon or the like.

In the second method, the amount of the at least one metal of the third fluorination catalyst is preferably from 0.1 to 20 wt % and more preferably from 1 to 10 wt %, based on the total weight of the carrier. It is optional to add an additive that is at least one element of alkali-earth metals such as Mg and Ca and lanthanide series elements such as La and Ce, to the third fluorination catalyst. This additive prevents recrystallization of an oxyhalide used as the at least one metal or as the carrier, thereby maintaining activity of the third fluorination catalyst. Weight ratio of the at least one metal to the additive is preferably from 50:50 to 99.9:0.1 and more preferably from 70:30 to 99:1.

In the second method, at least one metal compound used for preparing the third fluorination catalyst may be at least one of nitrate, chloride, oxide and the like of the at least one metal, which is soluble in a solvent such as water, ethanol, or acetone. Examples of the at least one metal compound are chromium nitrate, chromium trichloride, chromium trioxide, potassium dichromate, manganese nitrate, manganese chloride, manganese dioxide, nickel nitrate, nickel chloride, cobalt nitrate, and cobalt chloride.

In the second method, compositional change of the fluorination catalyst during the fluorination can effectively be prevented by treating, prior to the fluorination, either of the first, second and third fluorination catalysts with a fluorination agent such as hydrogen fluoride, fluorohydrocarbon or fluorochlorohydrocarbon, at a temperature not lower than the reaction temperature of the fluorination. The fluorination catalyst can effectively be prolonged in lifetime, and furthermore conversion and yield of the fluorination can effectively be improved, by supplying the reactor with oxygen, chlorine, fluorohydrocarbon or fluorochlorohydrocarbon, during the fluorination.

In the second method, when either of the first and second fluorination catalysts is used, the reaction temperature is preferably from 200 to 500° C. and more preferably from 250 to 400° C. When the third fluorination catalyst is used, the reaction temperature is preferably from 100 to 450° C. and more preferably from 150 to 300° C. If the reaction temperature is too low, the reaction rate may become impractically slow. If the reaction temperature is too high, the reaction rate becomes high. With this, however, the fluorination catalyst may become short in lifetime. Furthermore, there may be produced the decomposition products, excessively fluorinated products, and the like, and thus selectivity of 1-chloro-3,3,3-trifluoropropene may be lowered.

In the second method, ratio by mol of 1,1,1,3,3-pentachloro-propane to hydrogen fluoride varies depending on the reaction temperature. This ratio is preferably from 1/50 to 1/3 and more preferably from 1/10 to 1/3. If the amount of hydrogen fluoride is too large, the amount of the reaction product contained in the unit volume of the gas released from the reactor may become small. Furthermore, it may become difficult to separate the reaction product from a mixture of the reaction products and the unreacted hydrogen fluoride released from the reactor. If the amount of hydrogen fluoride is too small, conversion may become low, thereby lowering yield of the reaction product. However, even if the amount of hydrogen fluoride is too much or too little, that is not critical to the fluorination of large scale, because low-fluorinated compounds, unreacted substances, and/or hydrogen fluoride, which usually accompanies the reaction product, is separated from the reaction product and is reused.

In the second method, the reaction pressure is not particularly s limited. It is preferably from 1 to 10 kg/cm² from the viewpoint of the selection of the reactor material. It is preferable to select a reaction condition in which 1,1,1,3,3-pentachloropropane, intermediate products and hydrogen fluoride, which exist in the reaction system, are not liquefied in the reaction system. The contact time of the fluorination between 1,1,1,3,3-pentachloropropane and hydrogen fluoride is preferably from 0.1 to 300 seconds, and more preferably from 5 to 100 seconds.

The reactor's material used in the second method is not particularly limited, as long as the reactor has a sufficient heat resistance and a sufficient corrosion resistance against hydrogen fluoride, hydrogen chloride and the like. It is preferably stainless steel, Hastelloy, Monel metal or platinum, or a material lined with one of these metals.

In the second method, the reaction products containing 1-chloro-3,3,3-trifluoropropene may be purified by a conventional purification process that is not particularly limited. In this process, for example, the reaction products are washed with water and/or basic solution to remove acid substances such as hydrogen chloride and hydrogen fluoride. Then, the washed reaction products are dried and then distilled to remove organic impurities.

The first aspect of the present invention will be illustrated with reference to the following nonlimitative Examples 1–4.

EXAMPLE 1

In this example, 1,1,1,3,3-pentafluoropropane was prepared from 1-chloro-3,3,3-trifluoropropene, as follows, in accordance with the first method of the present invention.

At first, 0.05 mol (15.0 g) of antimony pentachloride (catalyst) and 0.6 mol (12 g) of hydrogen fluoride were introduced into a 1-liter autoclave made of stainless steel (SUS 316) and equipped with a reflux condenser, a pressure regulating valve, and a stirrer. Then, the autoclave's temperature was increased, while this mature was stirred. Then, hydrogen chloride produced by a reaction between antimony pentachloride and hydrogen fluoride was removed from the autoclave. After that, the autoclave was cooled down with ice, and then 0.5 mol (64.1 g) of 1-chloro-3,3,3-trifluoropropene was added to the autoclave. Then, temperature of the autoclave's inside was increased to 80° C., while the reaction mixture was stirred. At this temperature, the autoclave's inside pressure was maintained at 6 kg/cm²G for 3 hr, while the gas component was removed from the autoclave through the reflux condenser. The effluent was allowed to flow through a water layer and then through a concentrated sulfuric acid layer, and was condensed and collected in a trap previously cooled down by dry ice and methanol. After the reaction, the content of the autoclave was purged by reducing the inside pressure and was collected in the same way as during the reaction. Thereby, 37.2 g of an organic matter was obtained as a whole. By analysis with a gas chromatograph, it was found that this organic matter contains 57.9 mol % of 1,1,1,3,3-pentafluoropropane, 5.0 mol % of 1-chloro-3,3,3-trifluoropropene, 10.7 mol % of 1,1,3-tetrafluoro-3-chloropropane, and 26.4 mol % of 1,1,1-trifluoro-3,3-dichloropropane.

EXAMPLE 2

In this example, 1,1,1,3,3-pentafluoropropane was prepared from 1,1,1,3-tetrafluoro-3-chloropropane, as follows.

At first, 0.1 mol (29.9 g) of antimony pentachloride (catalyst) was introduced into a 1-liter autoclave that is the same as that used in Example 1. Then, the autoclave was cooled down with ice, and then 1.0 mol (149.7 g) of 1,1,1,3-tetrafluoro-3-chloropropane was added to the autoclave. Then, the autoclave's inside temperature was increased to 80° C., while the reaction mixture was stirred. At this temperature, the autoclave's inside pressure was maintained at 6 kg/cm²G for 3 hr by removing the gas component from the autoclave through the reflux condenser. Then, the gas component was subjected to the same treatments as those of Example 1. With this, 94.5 g of an organic matter was obtained. By analysis with a gas chromatograph, it was found that this organic matter contains 57.4 mol % of 1,1,1,3,3-pentafluoropropane, 6.0 mol % of 1-chloro-3,3,3-trifluoropropene, 12.4 mol % of 1,1,1,3-tetrafluoro-3-chloropropane, and 23.2 mol % of 1,1,1-trifluoro-3,3-dichloropropane.

EXAMPLE 3

In this example, Example 2 was repeated except in that 0.1 mol of antimony pentachloride was replaced by 0.05 mol (6.7 g) of aluminum chloride. The collected organic matter was in an amount of 103.1 g. By analysis with a gas chromatograph, it was found that this organic matter contains 42.4 mol % of 1,1,1,3,3-pentafluoropropane, 37.2 mol % of 1-chloro-3,3,3-trifluoropropene, 3.2 mol % of 1,1,1,3-tetrafluoro-3-chloropropane, and 17.2 mol % of 1,1,1-trifluoro-3,3-dichloropropane.

EXAMPLE 4

In this example, 1,1,1,3-tetrafluoro-3-chloropropane was prepared from 1-chloro-3,3,3-trifluoropropene, as follows.

At first, 0.05 mol (12.5 g) of boron tribromide (catalyst) and 0.65 mol (13 g) of hydrogen fluoride were introduced into a 1-liter autoclave that is the same as that of Example 1. Then, the autoclave's temperature was increased, while the reaction mixture was stirred. Then, hydrogen bromide produced by a reaction between boron tribromide and hydrogen fluoride was removed from the autoclave. After that, the autoclave was cooled down with ice, and then 0.5 mol (64.1 g) of 1-chloro-3,3,3-trifluoropropene was added to the autoclave. Then, temperature of the autoclave's inside was increased to 80° C., while the reaction mixture was stirred. At this temperature, the autoclave's inside pressure was maintained at 6 kg/cm²G for 6 hr, while the gas component was removed from the autoclave through the reflux condenser. The gas component was subjected to the same treatments as those of Example 1. With this, 63.9 g of an organic matter was obtained. By analysis with a gas chromatograph, it was found that this organic matter contains 90.7 mol % of 1,1,1,3-tetrafluoro-3-chloropropane and 9.3 mol % of 1-chloro-3,3,3-trifluoropropene.

The second aspect of the present invention will be illustrated with reference to the following nonlimitative Examples 5–18.

EXAMPLE 5

In this example, 1-chloro-3,3,3-trifluoropropene was produced by fluorinating 1,1,1,3,3-pentachloropropane with hydrogen fluoride in a gas phase in the presence of the first fluorination catalyst, as follows.

The first fluorination catalyst was prepared as follows. At first, 300 g of an active alumina in the form of sphere that is made by SUMITOMO CHEMICAL CO., LTD. and has a trade name of NKH3-24, a diameter of from 2 to 4 mm, a specific surface area of 340 m²/g and a morphological property of γ-alumina was washed with water to remove a powder attached to the surface of the active alumina. Separately, 10% hydrofluoric acid solution was prepared by dissolving 115 g of anhydrous hydrogen fluoride into 1,035 g of water. Then, the hydrofluoric acid solution was gradually poured on the active alumina. After stirring, this mixture was allowed to stand still for 3 hr. After that, the active alumina separated from the solution was washed with water, then was separated from water by filtration, and then was dried at 200° C. for 2 hr in an electric furnace. Then, 150 cc of the dried active alumina was put into a stainless steel reaction tube having an inner diameter of 1 inch and an axial length of 30 cm. Then, this reaction tube was put into the electric furnace, and then the electric furnace temperature was increased to 200° C, while nitrogen gas was allowed to flow through the reaction tube. After that, hydrogen fluoride gas together with nitrogen gas was allowed to flow therethrough to treat the active aluminum with hydrogen fluoride. As this treatment proceeded, the temperature of catalyst increased. In this treatment, flow rates of nitrogen and hydrogen fluoride were respectively adjusted such that the temperature of catalyst did not exceed 400° C. After this exothermic reaction of the active aluminum with hydrogen fluoride has finished, the reaction tube was further kept in the electric furnace at 400° C. for 2 hr.

Then, a cylindrical reaction tube for conducting a gas phase reaction was charged with 150 cc of the above-treated active aluminum.

This reaction tube was equipped with an electric furnace and was made of stainless steel (SUS316L) and had a diameter of 1 inch and an axial length of 30 cm. The reaction tube temperature was increased to 300° C., while nitrogen gas was allowed to flow therethrough at a flow rate of about 160 cc/min. After the temperature rose to 300° C., hydrogen fluoride gas was allowed to flow therethrough at a flow rate of about 0.20 g/min, together with nitrogen gas. Under this condition, the reaction tube temperature was increased to a maximum temperature of 350° C. and then was maintained at this temperature for 1 hr. Then, the reaction tube temperature was lowered to 250° C., and then the reaction (fluorination) was started by supplying the reaction tube with 1,1,1,3,3-pentachloropropane that had previously been vaporized, at a flow rate of 0.27 g/min, as shown in Table 1. 1 hr after the start of the reaction, the reaction became stable. After that, the reaction products (gas) released from the reaction tube were bubbled into water to remove an acid gas therefrom and then were collected by a trap cooled in dry ice and acetone. With this, 17.8 g of an organic matter was obtained. This organic matter was analyzed with a gas chromatograph, and the results of this analysis are shown in Table 2. In each of this example and the after-mentioned Examples 6–14, the rest of the organic matter, except 1,3,3,3-tetrafluoropropene, 1,1,1,3,3-pentafluoropropane and 1-chloro-3,3,3-trifluoropropene which are mentioned in Table 2, was an unidentified substance(s).

TABLE 1

|  | Reaction Temp. (° C.) | Reactants Flow Rates (g/min) | |
| --- | --- | --- | --- |
|  |  | 1,1,1,3,3-pentachloropropane | Hydrogen Fluoride |
| Example 5 | 250 | 0.27 | 0.29 |
| Example 6 | 250 | 0.56 | 0.19 |
| Example 7 | 300 | 0.56 | 0.19 |
| Example 8 | 350 | 0.56 | 0.19 |
| Example 9 | 400 | 0.56 | 0.19 |
| Example 10 | 250 | 1.01 | 0.40 |
| Example 11 | 300 | 1.01 | 0.40 |
| Example 12 | 250 | 1.01 | 0.40 |
| Example 13 | 300 | 1.01 | 0.40 |
| Example 14 | 350 | 1.01 | 0.40 |

TABLE 2

|  | Reaction Products Weight (g) | Chemical Composition of Reaction Products (mol %) | | |
| --- | --- | --- | --- | --- |
|  |  | 1,3,3,3-tetrafluoropropane | 1,1,1,3,3-pentafluoropropane | 1-chloro-3,3,3-trifluoropropane |
| Example 5 | 17.8 | 1.2 | 0.9 | 96.1 |
| Example 6 | 38.0 | 0.2 | 0.1 | 97.3 |
| Example 7 | 37.4 | 1.0 | 0.4 | 96.7 |
| Example 8 | 37.7 | 1.0 | 0.2 | 96.7 |
| Example 9 | 36.1 | 1.5 | 0.3 | 94.2 |
| Example 10 | 67.2 | 0.4 | 0.1 | 87.2 |
| Example 11 | 66.4 | 0.8 | 0.2 | 97.2 |
| Example 12 | 66.2 | 0.5 | 0.3 | 97.2 |
| Example 13 | 65.4 | 0.9 | 0.2 | 97.5 |
| Example 14 | 64.4 | 1.2 | 0.6 | 96.2 |

In these examples, Example 5 was repeated except in that the reaction conditions were modified as shown in Table 1. Only in Example 9, however, the reaction tube temperature was increased to a maximum of 400° C., in place of 350° C.

EXAMPLES 10–11

In these examples, Example 5 was repeated except in that the reaction conditions were modified as shown in Table 1 and that the nitrogen gas flow rate was modified into 320 cc/min.

EXAMPLE 12

In this example, 1-chloro-3,3,3-triuoropropene was produced by fluorinating 1,1,1,3,3-pentachloropropane with hydrogen fluoride in a gas phase in the presence of the second fluorination catalyst, as follows.

The second fluorination catalyst was prepared as follows. At first, 150 cc of pole rings each having a diameter of 5 mm and an axial length of 6 mm, which are used for a distillation tower and are made of stainless steel (SUS3 16L), was put into a stainless steel reaction tube having an inner diameter of 1 inch and an axial length of 30 cm. Then, this reaction tube was put into the electric furnace, and the electric furnace temperature was increased to 200° C., while nitrogen gas was allowed to flow through the reaction tube. After that, hydrogen fluoride gas together with nitrogen gas was allowed to flow therethrough to treat the pole rings with hydrogen fluoride. In this treatment, flow rates of nitrogen and hydrogen fluoride were respectively adjusted for 2 hr such that the furnace temperature did not exceed 400° C. With this, the second fluorination catalyst was prepared.

Then, a cylindrical reaction tube that is the same as that of Example 5 was charged with 150 cc of the above-prepared second fluorination catalyst. The reaction tube temperature was increased to 300° C., while nitrogen gas was allowed to flow therethrough at a flow rate of about 320 cc/min. Then, hydrogen fluoride gas was allowed to flow therethrough at a flow rate of about 0.40 g/min, together with nitrogen gas. Under this condition, the reaction tube temperature was increased to a maximum temperature of 350° C. and then was maintained at this temperature for 1 hr. Then, the reaction tube temperature was lowered to 250° C., and then the reaction (fluorination) was started by supplying the reaction tube with hydrogen fluoride at a flow rate of 0.40 g/min and with 1,1,1,1,3,3-pentachloropropane that had previously been vaporized, at a flow rate of 1.01 g/min, as shown in Table 1. 1 hr after the start of the reaction, the reaction became stable. After that, the reaction products were collected in a manner that is the same as that of Example 5. With this, 66.2 g of an organic matter was obtained. This organic matter was analyzed with a gas chromatograph, and the results of this analysis are shown in Table 2.

EXAMPLES 13–14

In these examples, Example 12 was repeated except in that the reaction temperature was modified as shown in Table 1.

EXAMPLE 15

In this example, 1-chloro-3,3,3-trifluoropropene was produced by fluorinating 1,1,1,3,3-pentachloropropane with hydrogen fluoride in a gas phase in the presence of the third fluorination catalyst, as follows.

The third fluorination catalyst was prepared as follows. At first, 1 liter of a $CrCl_3$ aqueous solution was prepared by dissolving 336 g of $CrCl_3.6H_2O$ into pure water. Into this solution, 250 cc of an active alumina having an average diameter of 5 mm and a surface area per unit weight of 340 $m^2/g$ was immersed, and then this solution was allowed to stand still for one day and one night. After that, the active alumina was separated from the solution by filtration, and then were dried for one day and one night at 100° C. in a hot-air circulating type oven. The thus obtained chromium-carried alumina was put into a cylindrical reaction tube that is equipped with an electric furnace and is made of stainless steel (SUS316L) and has a diameter of 5 cm and an axial length of 30 cm. The reaction tube temperature was increased to 300° C., while nitrogen gas was allowed to flow therethrough. Then, at the time when it was found that steam flow therefrom stopped, it was started to allow hydrogen fluoride to flow therethrough, together with nitrogen gas. Then, hydrogen fluoride concentration of the mixture of hydrogen fluoride and nitrogen was gradually increased. When a hot spot produced by fluorinating the chromium-carried alumina reached the end of exit of the reaction tube, the reaction tube temperature was further increased to 350° C. Then, this condition was maintained for 1 hr, thereby preparing the third fluorination catalyst.

Then, the fluorination was conducted as follows. At first, 50 cc of the above-prepared third fluorination catalyst was put into a cylindrical reaction tube that is the same as that of Example 5. Then, the reaction tube temperature was increased to 300° C., while nitrogen gas was allowed to flow therethrough at a flow rate of about 190 cc/min. Then, hydrogen fluoride gas was also allowed to flow therethrough at a flow rate of about 0.25 g /min, together with nitrogen gas. Then, the reaction tube temperature was increased to 350° C., and then this condition was maintained for 1 hr. Then, the reaction tube temperature was decreased to 220° C., and then the reaction (fluorination) was started by supplying the reaction tube with 1,1,1,3,3-pentachloropropane that had previously been vaporized, at a flow rate of 0.35 g/min, and with hydrogen fluoride at a flow rate of 0.29 g /min, as shown in Table 3. 1 hr after the start of the reaction, the reaction became stable. After that, the reaction products were collected in a manner that is the same as that of Example 5. The organic matter obtained above was analyzed with a gas chromatograph, and the results of this analysis are shown in Table 4.

TABLE 3

| | Reaction Temp. (° C.) | Reactants Flow Rates (g/min) | |
| --- | --- | --- | --- |
| | | 1,1,1,3,3-pentachloropropane | Hydrogen Fluoride |
| Example 15 | 220 | 0.35 | 0.29 |
| Example 16 | 200 | 0.30 | 0.25 |
| Example 17 | 150 | 0.27 | 0.24 |
| Example 18 | 800 | 0.28 | 0.27 |

TABLE 4

| | Nitrogen Gas Flow Rate (ml/min) | Yield of 1-chloro-3,3,3-trifluoropropene (%) | Purity of 1-chloro-3,3,3-trifluoropropene (%) |
| --- | --- | --- | --- |
| Example 15 | 190 | 95 | 97 |
| Example 16 | 170 | 86 | 97 |
| Example 17 | 185 | 82 | 86 |
| Example 18 | 185 | 84 | 84 |

EXAMPLES 16–18

In these examples, Example 15 was repeated except in that the 5 reaction conditions were modified as shown in Tables 3–4.

What is claimed is:

1. A method for producing 1,1,1,3,3-pentafluoropropane, comprising steps of:
   (a) adding hydrogen fluoride to 1-chloro-3,3,3-trifluoropropene in the presence of an addition catalyst to obtain 1,1,1,3-tetrafluoro-3-chloropropane; and
   (b) disproportionating said 1,1,1,3-tetrafluoro-3-chloropropane into said 1,1,1,3,3-pentafluoropropane and 1,1,1-trifluoro-3,3-dichloropropane, in the presence of a disproportionation catalyst.

2. A method for producing 1,1,1,3,3-pentafluoropropane, comprising a step of disproportionating 1,1,1,3-tetrafluoro- 3-chloropropane into said 1,1,1,3,3-pentafluoropropane and 1,1,1-trifluoro-3,3-dichloropropane, in the presence of a disproportionation catalyst.

3. A method according to claim 1, wherein said addition catalyst is at least one compound selected from the group consisting of antimony halides, tin halide, titanium halides, and boron halides.

4. A method according to claim 3, wherein said antimony halides are antimony pentahalides and antimony trihalides, said tin halides are tin tetrahalides, said titanium halides are titanium tetrahalides, and said boron halides are boron trihalides.

5. A method according to claim 4, wherein said antimony pentahalides are antimony pentachloride, antimony pentabromide, antimony pentaiodide and antimony pentafluoride, said antimony trihalides are antimony trichloride, antimony tribromide and antimony triiodide, said tin tetrahalides are tin tetrachloride, tin tetrabromide, tin tetraiodide and tin tetrafluoride, said titanium tetrahalides are titanium tetrachloride, titanium tetrabromide, titanium tetraiodide and titanium tetrafluoride, and said boron trihalides are boron trichloride, boron tribromide, boron triiodide and boron trifluoride .

6. A method according to claim 3, wherein said addition catalyst is at least one compound selected from the group consisting of antimony pentachloride, antimony trichloride, tin tetrachloride, titanium tetrachloride, and boron trifluoride.

7. A method according to claim 1, wherein said disproportionation catalyst is at least one compound selected from the group consisting of antimony halides and aluminum halides.

8. A method according to claim 7, wherein said antimony halides are antimony pentachloride, antimony pentabromide, antimony pentaiodide and antimony pentafluoride, and said aluminum halides are aluminum chloride, aluminum bromide and aluminum iodide.

9. A method according to claim 1, wherein said addition and disproportionation catalysts are identical and are respectively at least one compound selected from antimony halides.

10. A method according to claim 1, wherein said addition and disproportionation catalysts are respectively in an amount of from 0.1 to 50 mol %, based on the total number of moles of said 1-chloro-3,3,3-trifluoropropene.

11. A method according to claim 10, wherein said addition and disproportionation catalysts are respectively in an amount of from 2 to 20 mol % and in an amount of from 1 to 20 mol %, based on the total number of moles of said 1-chloro-3,3,3-trifluoropropene.

12. A method according to claim 1, wherein said hydrogen fluoride is in an amount of from about 1 part to about 2 parts by mol per 1 part by mol of said 1-chloro-3,3,3-trifluoropropene.

13. A method according to claim 1, wherein said step (a) is conducted at a temperature of from −10 to 150° C.

14. A method according to claim 1, wherein said step (b) is conducted at a temperature of from 0 to 150° C.

15. A method according to claim 1, wherein said 1-chloro-3,3,3-trifluoropropene is produced by a step of (c) reacting 1,1,1,3,3-pentachloropropane with hydrogen fluoride in a gas phase in the presence of a fluorination catalyst.

* * * * *